United States Patent
Penney

(10) Patent No.: US 6,188,278 B1
(45) Date of Patent: Feb. 13, 2001

(54) AMPLIFICATION CIRCUITS

(75) Inventor: Stephen John Penney, Northolt (GB)

(73) Assignee: Thorn Security Limited, Middlesex (GB)

(*) Notice: Under 35 U.S.C. 154(b), the term of this patent shall be extended for 0 days.

(21) Appl. No.: 09/261,238

(22) Filed: Mar. 3, 1999

(30) Foreign Application Priority Data

Mar. 3, 1998 (GB) .................................................. 9804514

(51) Int. Cl.⁷ .................................................. H03F 1/14
(52) U.S. Cl. .................................................. 330/51; 330/288
(58) Field of Search .................... 330/51, 288, 300, 330/311

(56) References Cited

U.S. PATENT DOCUMENTS

| | | | |
|---|---|---|---|
| 5,438,247 | * 8/1995 | Kim et al. | 73/619 |
| 5,625,281 | * 4/1997 | Lambert | 323/315 |
| 6,011,415 | * 1/2000 | Hahn et al. | 330/288 |

* cited by examiner

Primary Examiner—Robert Pascal
Assistant Examiner—Khanh Van Nguyen
(74) Attorney, Agent, or Firm—Evenson, McKeown, Edwards & Lenahan, P.L.L.C.

(57) ABSTRACT

An amplification circuit for use with an electro chemical cell is disclosed. The cell is operated in the amperometric mode and finds beneficial application in the detection of carbon monoxide (CO) gas. The amplification circuit of the invention is used to derive electrical output signals from the cell whilst ensuring that the cell electrodes are held at a potential that minimises cross-sensitivities and controlling voltage spikes which the cell would otherwise extend in duration, due to its capacitive behaviour, and comprises an operational amplifier connected to derive electrical output signals from the cell and having a feedback path incorporating at least one component of a current mirror circuit.

4 Claims, 1 Drawing Sheet

AMPLIFICATION CIRCUITS

BACKGROUND AND SUMMARY OF THE INVENTION

This invention relates to amplification circuits, and it relates especially, though not exclusively, to such circuits as may be used in association with electro chemical cells configured to detect carbon monoxide (CO), thereby to enable a warning as to the presence of the gas to be generated. As is known, the gas is harmful of itself, and it is also a typical product of fire. Thus its sensitive and reliable detection is valuable on at least two fronts.

Electro chemical cell technology is proving to be one of the most competent on which to build CO detectors, but the development and handling of the electrical signals generated by such detectors is associated with difficulty, inter alia because they are run in an amperometric mode, where it is critical (a) to hold the cell electrodes at the correct potential to minimise cross-sensitivities, and (b) to control voltage spikes which, due to the typically capacitive behaviour of such cells would be greatly amplified in duration.

It is an object of the present invention to provide a circuit which addresses the difficulty mentioned above.

According to the invention there is provided an amplification circuit intended for use in association with an electro chemical cell operated in amperometric mode, the circuit comprising an operational amplifier coupled to said cell so as to derive output signals therefrom, and a current mirror circuit having at least one component connected in a feedback path of said operational amplifier.

It has been proposed in GB-A-2307753 to utilise a current mirror circuit in association with an operational amplifier and an electrochemical cell. The circumstances envisaged in that proposal, however, differ substantially from the situation addressed by the present invention. In particular, the electro chemical cell is operated in impedance mode, and the current mirror circuit, which is not connected in the feedback path of the operational amplifier, is instead used in the amplifier's power supply and thus is not part of the path for output signals from the cell.

BRIEF DESCRIPTION OF THE DRAWINGS

In order that the invention may be clearly understood and readily carried into effect, one embodiment thereof will now be described, by way of example only, with reference to the accompanying drawings of which.

DETAILED DESCRIPTION OF THE DRAWINGS

Figure 1:
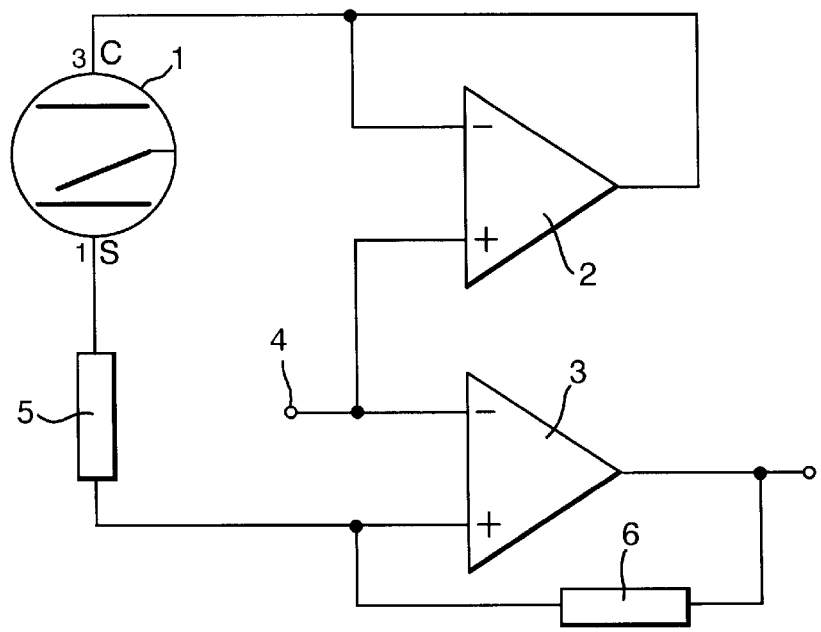
FIG. 1 shows, in simplified form, a conventional prior art circuit associated with an electrochemical cell operated in amperometric mode.

Referring to FIG. 1, an electro chemical cell 1 is coupled in conventional manner to amplification and processing circuitry including a pair of operational amplifiers 2 and 3. With this circuit, although the counter (C) and sensing (S) electrodes of the cel 1 are nominally held at the same potential, heavy reliance is placed upon the quality of the input stages of the operational amplifiers 2 and 3, to which latter the S electrode is connected via a low (22R) resistance 5. A resistor 6 is connected in known manner in the feedback path of amplifier 3.

In practice, with this circuit, expensive amplifiers must be used to ensure that significant bias differences between the two amplifiers do not introduce error currents into the output. Furthermore, amplifier 3 is typically of extremely high gain, so that changes in output loading, or gain resistance, may produce spurious effects.

By far the greatest problem with this kind of circuit, however, is that the two amplifiers 2 and 3 behave very differently in response to fluctuations in the pedestal voltage applied to terminal 4, due to the high capacitance of the cell 1. Thus a short voltage spike may be considerably extended in duration.

The circuit of the present invention isolates the cell's biassing circuitry from the circuit used to measure the current generated by the action of CO on the cell by connecting a modified current mirror in the feedback loop of an operational amplifier. The invention also makes it possible to effectively short-circuit the cell during unpowered periods, thus minimising the impact on detector power-up and reset times.

Figure 2:
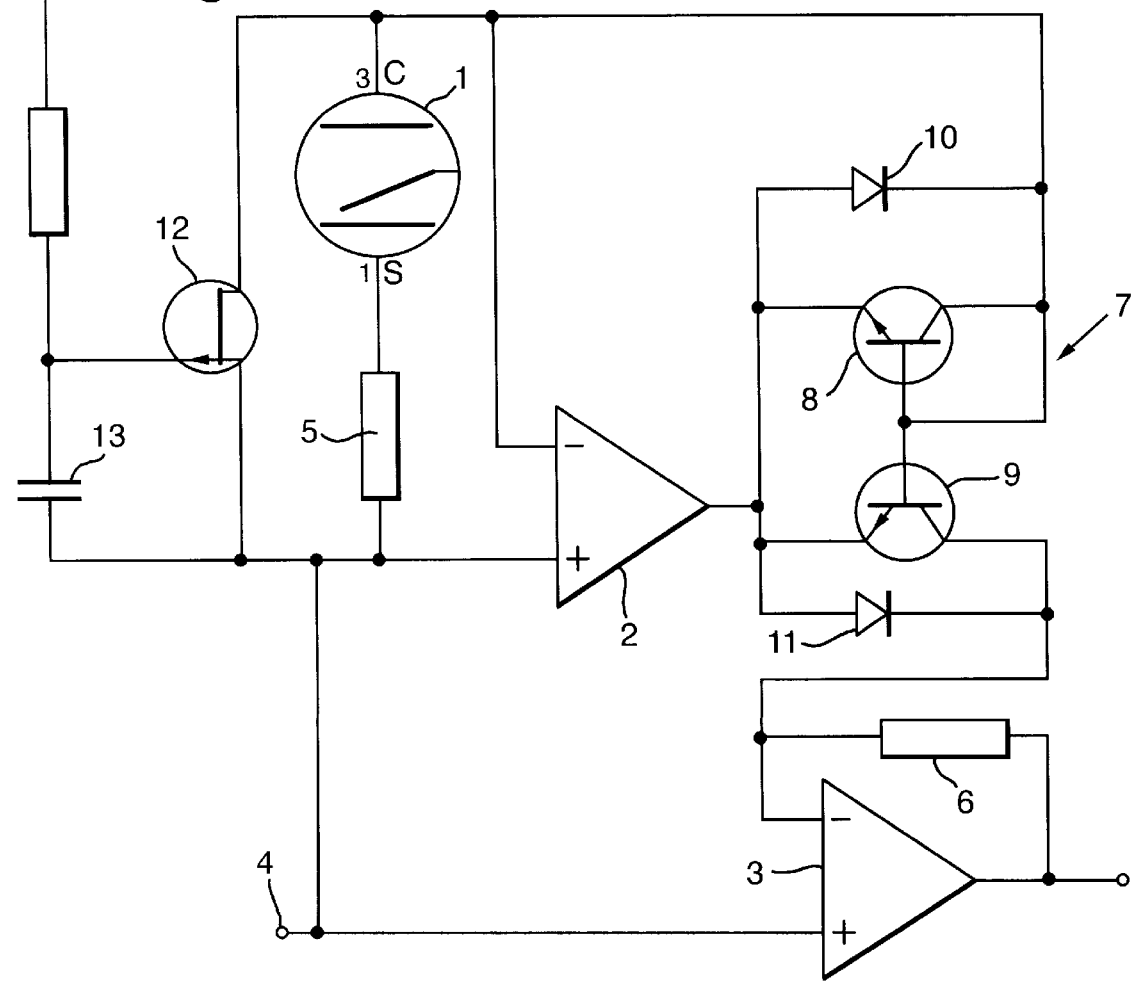
FIG. 2 shows, again in simplified and somewhat schematic form, such a cell coupled to a circuit in accordance with one example of the invention.

With reference now to FIG. 2, in which components common to FIG. 1 carry the same reference numerals (though it will be appreciated that the operational amplifiers shown in FIG. 2 may not be of the same specification as those identified by similar reference numbers in the prior art circuit shown in FIG. 1), the sensor (S) terminal of cel 1 is connected, via the small resistance 5, to the pedestal voltage applied to terminal 4. A current mirror circuit, generally shown at 7, is connected into the output of amplifier 2 and into its feedback loop. The mirror circuit 7 comprises a NPN transistor pair 8, 9 and a pair of diodes 10 and 11.

When the electrode S attempts to become more negative, this is balanced by amplifier 2 sinking current from the electrode C through transistor 8. Amplifier 3 then produces a voltage output proportional to the current flowing through transistor 9; this mirroring the current flowing through transistor 8, which is in the feedback loop of amplifier 2. The only standing current in the circuit is that attributable to the small input offset voltage at the inputs of amplifier 2. Moreover, voltage spikes superimposed on the pedestal voltage are effective only to lift the potential of the whole circuit, without creating differential signals that could be amplified.

Overall, the circuit is effective to match the feedback currents in the two amplifiers 2 and 3, whilst isolating amplifier 2 from offset bias, loading, and matching problems associated with amplifier 3. The diodes 10 and 11 modify the current mirror circuit to allow current to flow in the reverse direction, thus preventing voltage changes which would otherwise occur should electro chemical variations generate a slightly positive signal at the S electrode of cell 1.

A further advantageous feature of the circuit shown in FIG. 2 is that very high or low excursions of the output from amplifier 2 at start-up, which could occur as a result of amplification of the initial offset bias, are suppressed because the field effect transistor 12 continues to short-circuit the amplifier's inputs until the capacitor 13 has developed sufficient charge to turn the transistor 12 off The turning-off of the transistor 12, moreover, occurs gradually and hence the cell 1 is not subjected to sudden changes on start-up. Accordingly, the settling time of the circuit is acceptably short.

The normal response of the cell 1 to the detection of CO is to generate a current flowing from the C to the S electrode, and the current mirror transistor polarity, and that of the diodes 10 and 11, is set up for such operation. If, however, the circuit were to be used for the sensing of other gases causing the cell to generate a current of the opposite polarity, the operation of the diode and transistor components of the current mirror circuit 7 could be reversed.

In the event of the cell requiring a bias potential for sensing gases other than CO, this can conveniently be supplied by means of a differential voltage applied between the electrode C of cell 1 and the feedback loop.

It will be appreciated that the present invention permits at least the following functional benefits to be obtained:

(i) The cell electrodes are held at the optimum potential for sensing CO;

(ii) Variation of the pedestal voltage does not significantly affect the potential difference between the electrodes of the electro chemical cell, rendering the sensor acceptably resistant to electrical noise;

(iii) Variations on the impedance loading of the measurement circuit do not significantly affect the cell biassing circuit;

(iv) The input offset voltage of one only of the operational amplifiers principally determines the electrode potentials;

(v) Cell background current can be of either polarity without significantly affecting the electrode potentials;

(vi) There is no requirement for additional operational amplifiers to buffer circuit output signals prior to setting the detector's sensitivity level; and (vii) The sensor's current path is maintained, even when no power is present.

Although reference has been made, in the embodiment described, to a pair of transistors, variations to the embodiment may be made. For example, other components having the same characteristics or capable of performing the same function may be used instead of the transistor pair. Such components include two pairs of transistors or a single component matched device or an ASIC device or any suitable component performing an equivalent "current mirroring" task as the transistors in the current mirror circuit.

What is claimed is:

1. An amplification circuit intended for use in association with an electro chemical cell operated in amperometric mode, the circuit comprising an operational amplifier coupled to said cell so as to derive output signals therefrom, and a current mirror circuit having at least one component connected in a feedback path of said operational amplifier, wherein said current mirror circuit comprises a pair of transistors, one of which comprises said at least one component, and wherein said current mirror circuit further comprises a respective unidirectionally conductive device connected across the collector-emitter path of each said transistors.

2. An amplification circuit intended for use in association with an electro chemical cell operated in amperometric mode, the circuit comprising an operational amplifier coupled to said cell so as to derive output signals therefrom, and a current mirror circuit having at least one component connected in a feedback path of said operational amplifier, and comprising a further operational amplifier coupled to receive output signals from the first-mentioned operational amplifier and configured to provide an output signal from said circuit.

3. A circuit according to claim 2 wherein said operational amplifiers operate at different pedestal voltages.

4. An amplification circuit intended for use in association with an electro chemical cell operated in amperometric mode, the circuit comprising an operational amplifier coupled to said cell so as to derive output signals therefrom, and a current mirror circuit having at least one component connected in a feedback path of said operational amplifier, and further including a field effect transistor connected to short-circuit operative electrodes of said cell and coupled to capacitive means arranged to accumulate charge when a power supply for said cell is energized, the arrangement being such that the rate of accumulation of said charge by said capacitive means causes a gradual turning-off of said field-effect transistor and hence removal of said short-circuit.

* * * * *